United States Patent
Shido et al.

(10) Patent No.: US 12,422,393 B2
(45) Date of Patent: Sep. 23, 2025

(54) GAS SENSOR, GAS SENSOR ASSEMBLY, AND CHEMICAL SUBSTANCE IDENTIFICATION METHOD

(71) Applicant: Panasonic Intellectual Property Management Co., Ltd., Osaka (JP)

(72) Inventors: Chiaki Shido, Kyoto (JP); Yosuke Hanai, Osaka (JP); Atsuo Nakao, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 345 days.

(21) Appl. No.: 18/017,994

(22) PCT Filed: Aug. 5, 2021

(86) PCT No.: PCT/JP2021/029095
§ 371 (c)(1),
(2) Date: Jan. 25, 2023

(87) PCT Pub. No.: WO2022/030574
PCT Pub. Date: Feb. 10, 2022

(65) Prior Publication Data
US 2023/0349850 A1 Nov. 2, 2023

(30) Foreign Application Priority Data
Aug. 5, 2020 (JP) .................. 2020-133031

(51) Int. Cl.
*G01N 27/12* (2006.01)
*G01N 33/00* (2006.01)

(52) U.S. Cl.
CPC ......... *G01N 27/125* (2013.01); *G01N 27/126* (2013.01); *G01N 33/0027* (2013.01)

(58) Field of Classification Search
CPC .... G01N 27/12; G01N 27/125; G01N 27/126; G01N 33/0027; G01N 33/0031
See application file for complete search history.

(56) References Cited

U.S. PATENT DOCUMENTS

2006/0027098 A1* 2/2006 Lautamo ............... C08G 77/50
95/82
2007/0178600 A1 8/2007 Lebret et al.
(Continued)

FOREIGN PATENT DOCUMENTS

| JP | 06-160317 A | 6/1994 |
|---|---|---|
| JP | 2007-513347 A | 5/2007 |
| JP | 2016-017937 A | 2/2016 |

(Continued)

OTHER PUBLICATIONS

International Search Report issued on Oct. 19, 2021 in International Patent Application No. PCT/JP2021/029095, with English translation.

*Primary Examiner* — Benjamin R Schmitt
(74) *Attorney, Agent, or Firm* — Rimon P.C.

(57) ABSTRACT

A gas sensor includes: a sensing unit; and a first electrode and a second electrode that are a pair of electrodes each electrically connected to the sensing unit. The sensing unit has a conductive material and a polymer having a siloxane bond as a main chain structure. The polymer has a cyano group in a side chain.

19 Claims, 7 Drawing Sheets

(56) References Cited

U.S. PATENT DOCUMENTS

2018/0364204 A1    12/2018  McCauley
2020/0033283 A1    1/2020   Nakao et al.

FOREIGN PATENT DOCUMENTS

| WO | WO-2018186268 A1 * | 10/2018 | ............. G01N 27/12 |
| WO | 2019/172251 A1 | 9/2019 | |
| WO | WO-2019189245 A1 * | 10/2019 | ............. G01N 27/12 |

* cited by examiner

GAS SENSOR, GAS SENSOR ASSEMBLY, AND CHEMICAL SUBSTANCE IDENTIFICATION METHOD

CROSS-REFERENCE OF RELATED APPLICATIONS

This application is the U.S. National Phase under 35 U.S.C. § 371 of International Patent Application No. PCT/JP2021/029095, filed on Aug. 5, 2021, which in turn claims the benefit of Japanese Patent Application No. 2020-133031, filed on Aug. 5, 2020, the entire disclosures of which Applications are incorporated by reference herein.

TECHNICAL FIELD

The present disclosure relates to a gas sensor, a gas sensor assembly, and a chemical substance identification method.

BACKGROUND ART

There has been known a gas sensor that detects a chemical substance, such as a volatile organic compound, in a gas by detecting a characteristic of a sensing unit having an adsorbent made of a polymer or the like as a result of the adsorption of the chemical substance on the sensing unit (for example, Patent Literature (PTL) 1 and 2).

CITATION LIST

Patent Literature

[PTL 1] WO 2019/172251
[PTL 2] WO 2018/186268

SUMMARY OF INVENTION

Technical Problem

In a case where a gas sensor is used to identify a chemical substance such as a volatile organic compound, an odor, or the like in a gas, a gas sensor with high identification accuracy is required.

The present disclosure provides a gas sensor and the like that can improve identification accuracy when used to identify a chemical substance or the like.

Solution to Problem

A gas sensor according to one aspect of the present disclosure includes: a sensing unit; and a pair of electrodes each electrically connected to the sensing unit. The sensing unit has a conductive material and a polymer having a siloxane bond as a main chain structure, and the polymer has a cyano group in a side chain.

A gas sensor assembly according to one aspect of the present disclosure includes a plurality of gas sensors, and at least one of the plurality of gas sensors is the gas sensor described above.

A chemical substance identification method according to one aspect of the present disclosure is a chemical substance identification method using the gas sensor assembly described above, the method including: obtaining a signal output from the gas sensor assembly exposed to a gas containing a chemical substance; calculating a feature from the signal obtained; and identifying the chemical substance contained in the gas based on the feature calculated.

Advantageous Effects

The gas sensor and the like according to one aspect of the present disclosure can improve identification accuracy when used to identify a chemical substance or the like.

Figure 1:
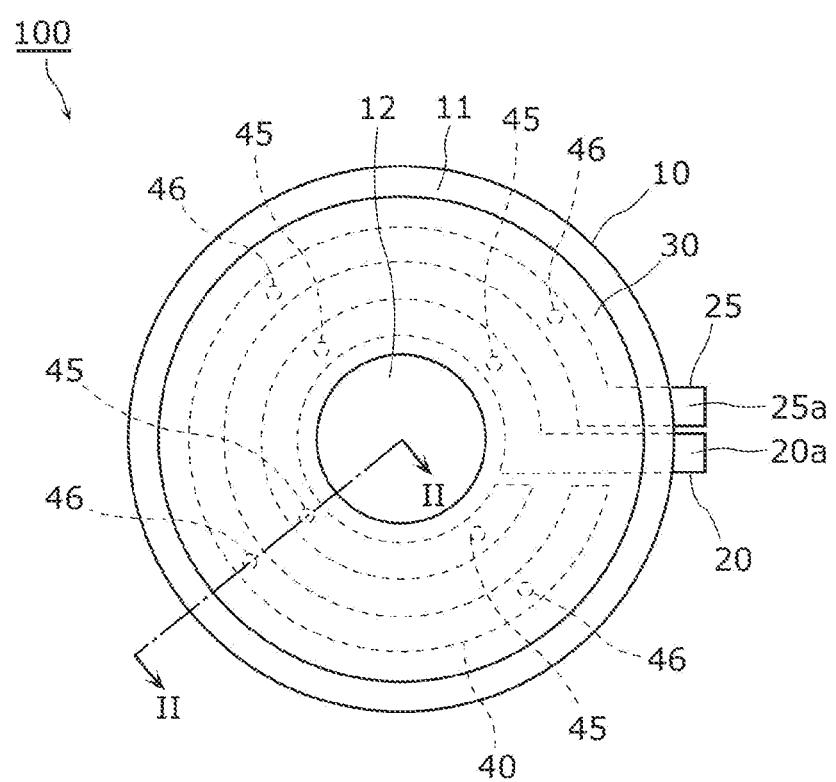
FIG. 1 is a plan view illustrating a schematic configuration of a gas sensor according to an embodiment.

DESCRIPTION OF EMBODIMENT (Underlying Knowledge Forming Basis of the Present Disclosure)

In a gas sensor provided with a sensing unit having an adsorbent or the like, for example, as the sensing unit adsorbs a chemical substance in a gas and expands, the electrical characteristic, such as the electrical resistance, of the sensing unit changes. The electrical characteristic such as the electrical resistance is detected using an electrode electrically connected to the sensing unit to detect the chemical substance in the gas.

PTL 1 discloses a chemical sensor element provided with a detection material containing a polysiloxane compound. In a case where a polysiloxane compound is used as the adsorbent of the sensing unit of the gas sensor as in the chemical sensor element described in the example of PTL 1, for example, a polysiloxane compound having a hydrocarbon group, such as a methyl group or a phenyl group, in a side chain is used as the adsorbent. However, when the gas sensor provided with the sensing unit containing the polysiloxane compound having the hydrocarbon group in the side chain as the adsorbent is used to identify chemical substances, some chemical substances are difficult to identify by the gas sensor. The present inventors have found that, when the gas sensor provided with the sensing unit containing the polysiloxane compound having the hydrocarbon group in the side chain as the adsorbent is used to identify chemical substances, the identification accuracy for a hydrogen bond acceptor molecule among the chemical substances is high, but the identification accuracy for a hydrogen bond donor molecule is low. The identification accuracy for the chemical substance by the gas sensor is considered to be related to the magnitude of a change in the electrical characteristic of the sensing unit. For example, when the interaction between the hydrogen bond donor molecule and the sensing unit is weak, the hydrogen bond donor molecule is hardly adsorbed onto the sensing unit. As a result, the change in the electrical characteristic of the sensing unit is small, and the identification accuracy is considered to be low when the gas sensor is used to identify the hydrogen bond donor molecule.

Therefore, the present disclosure provides a gas sensor that can improve identification accuracy by improving identification accuracy for a hydrogen bond donor molecule when used to identify a chemical substance or the like.

Overview of the Present Disclosure

An overview of one aspect of the present disclosure is as follows.

A gas sensor according to one aspect of the present disclosure includes: a sensing unit; and a pair of electrodes each electrically connected to the sensing unit. The sensing unit has a conductive material and a polymer having a siloxane bond as a main chain structure, and the polymer has a cyano group in a side chain.

This makes it easier for the cyano group to interact with the hydrogen bond donor molecule because the cyano group is a hydrogen bond acceptor. As a result, when the gas contains hydrogen bond donor molecules, the electrical characteristic, such as the electrical resistance, of the sensing unit is likely to change. Therefore, the gas sensor can improve identification accuracy when used to identify a chemical substance or the like.

For example, the polymer may have an alkylene group located between the cyano group and the main chain in the side chain.

By the alkylene group being located between the cyano group and the main chain, the cyano group can be separated from the main chain of the polysiloxane compound, thus making it easier for the cyano group to interact with the hydrogen bond donor molecule. It is thus possible to further improve identification accuracy when the gas sensor is used to identify the chemical substance or the like.

For example, the polymer may have a cyanopropyl group in the side chain.

Thereby, the distance between the main chain and the cyano group in the polymer is maintained appropriately, so that it is possible to achieve a gas sensor having both the stability of the polysiloxane compound and the identification accuracy when used to identify the chemical substance or the like.

For example, the polymer may have at least one structure selected from the group consisting of a biscyanopropylpolysiloxane structure, a cyanopropylmethyl-dimethylpolysiloxane structure, a biscyanopropyl-cyanopropylphenylpolysiloxane structure, a cyanopropylphenyl-dimethylpolysiloxane structure, and a cyanopropylmethyl-phenylmethylpolysiloxane structure.

Thus, the sensing unit can be achieved using a polymer that is easy to synthesize.

For example, in the thermogravimetric analysis of the polymer in an air atmosphere, a temperature at which a weight of the polymer decreases by 5% or more relative to the weight of the polymer at 35° C. may be 250° C. or higher.

Hence the polymer has excellent thermal stability, making the detection accuracy of the gas sensor less likely to deteriorate over time For example, a detector that detects the electric resistance of the sensing unit may be further provided.

Thus, the gas sensor can detect the electric resistance to detect the chemical substance or the like and can use the detected electric resistance to identify the chemical substance or the like.

For example, the conductive material is conductive particles, and an average particle size of the conductive particles may be in the range of 10 nm to 300 nm, inclusive.

Thereby, the electrical characteristic, such as the electrical resistance, of the sensing unit is likely to change.

For example, the ratio of the weight of the conductive material to the weight of the sensing unit may be in the range of 0.05 to 0.95, inclusive.

This allows a current to flow easily through the sensing unit and can thus facilitate the detection of the electrical characteristic, such as the electrical resistance, of the sensing unit.

For example, the sensing unit is film-shaped.

Thereby, when the chemical substance is adsorbed onto the sensing unit, the electrical characteristic is likely to change.

A gas sensor assembly according to one aspect of the present disclosure includes a plurality of gas sensors, and at least one of the plurality of gas sensors is the gas sensor described above.

Hence the gas sensor assembly includes the gas sensor described above, thus making it possible to improve identification accuracy when the gas sensor assembly is used to identify the chemical substance or the like.

A chemical substance identification method according to one aspect of the present disclosure is a chemical substance identification method using the gas sensor assembly described above, the method including: obtaining a signal output from the gas sensor assembly exposed to a gas containing a chemical substance; calculating a feature from the signal obtained; and identifying the chemical substance contained in the gas based on the feature calculated.

Hence the chemical substance can be identified with high accuracy using the gas sensor assembly.

Note that an exemplary embodiment described below shows a comprehensive or a specific example. Numerical values, shapes, materials, components, arrangement and connection modes of the components, steps, the order of the steps, and the like, which will be shown in the following embodiment, are only examples and are not intended to limit the present disclosure. Among the components in the following embodiment, components not recited in independent claims are described as optional components.

In the present specification, a term indicating a relationship between elements, such as parallel, a term indicating the shape of an element, and a numerical range are not expressions expressing only strict meanings but expressions meaning to include substantially equivalent ranges, for example, differences of about a few percent.

Each of the drawings is not necessarily strictly illustrated. In the drawings, substantially the same components are denoted by the same reference numerals, and duplicated description is omitted or simplified.

In the present specification, the term "plan view" means a case where the gas sensor is viewed along the thickness direction of the substrate (in other words, the direction normal to the main surface of the substrate).

Further, in the present specification, the term "upward (or above)" or "downward (or below)" does not refer to an up direction (for example, vertically upward (or above)) or a down direction (for example, vertically downward (or below)) in absolute space recognition, but is used as a term defined by a relative positional relationship based on the arrangement configuration of each component member on the substrate.

EMBODIMENT

First, a gas sensor according to an embodiment will be described.

Figure 2:
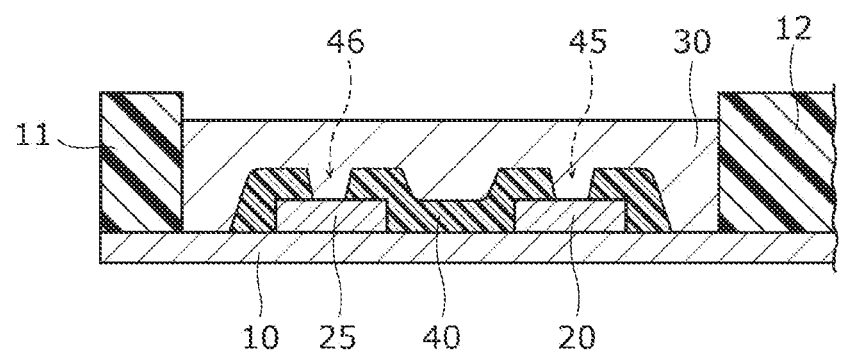
FIG. 2 is a cross-sectional view of the gas sensor according to the embodiment at a position indicated by line II-II in FIG. 1.

FIG. 1 is a plan view illustrating a schematic configuration of a gas sensor according to the present embodiment. FIG. 2 is a cross-sectional view of the gas sensor according to the present embodiment at a position indicated by line II-II in FIG. 1.

As illustrated in FIGS. 1 and 2, gas sensor 100 according to the present embodiment includes substrate 10, first electrode 20 and second electrode 25, which are a pair of electrodes, sensing unit 30, and insulating layer 40. In FIG. 1, the shapes of first electrode 20 and second electrode 25 covered with sensing unit 30 and insulating layer 40 in plan view are indicated by broken lines.

Substrate 10 is a substrate for supporting first electrode 20, second electrode 25, insulating layer 40, and sensing unit 30. Substrate 10 is, for example, plate-shaped. Substrate 10 has, for example, a rectangular or circular shape in plan view. In the present embodiment, substrate 10 has a circular shape in plan view. The material of substrate 10 is not particularly limited as long as being able to maintain the shape of gas sensor 100. Substrate 10 is, for example, a silicon substrate, a metal plate, a glass plate, a polymer film, or the like.

First electrode 20 is disposed on substrate 10. The lower surface of first electrode 20 is in contact with the upper surface of substrate 10. The shape of first electrode 20 is not particularly limited. First electrode 20 has, for example, an arc shape or a ring shape in plan view. In the present embodiment, first electrode 20 has an arc shape in plan view and also has a band shape.

First electrode 20 includes terminal 20a exposed outside of gas sensor 100. In FIG. 1, terminal 20a extends beyond the outer peripheral surface of substrate 10 to the outside of substrate 10. Note that first electrode 20 may not have a portion extending beyond the outer peripheral surface of substrate 10 to the outside of substrate 10. For example, a through hole may be provided in substrate 10, and a part of the lower surface of first electrode 20 may be exposed outside of gas sensor 100 through the through hole. In this case, a part of the lower surface of first electrode 20 corresponds to terminal 20a.

Second electrode 25 is disposed on substrate 10. The lower surface of second electrode 25 is in contact with the upper surface of substrate 10. The shape of second electrode 25 is not particularly limited. Second electrode 25 surrounds first electrode 20, for example. Second electrode 25 is not in contact with first electrode 20. Second electrode 25 has, for example, an arc shape or a ring shape in plan view. In the present embodiment, second electrode 25 has an arc shape in plan view and also has a band shape.

Second electrode 25 includes terminal 25a exposed outside of gas sensor 100. In FIG. 1, terminal 25a extends beyond the outer peripheral surface of substrate 10 to the outside of substrate 10. Note that second electrode 25 may not have a portion extending beyond the outer peripheral surface of substrate 10 to the outside of substrate 10. For example, a through hole may be provided in substrate 10, and a part of the lower surface of second electrode 25 may be exposed outside of gas sensor 100 through the through hole. In this case, a part of the lower surface of second electrode 25 corresponds to terminal 25a.

Of first electrode 20 and second electrode 25, which are a pair of electrodes, first electrode 20 is electrically connected to sensing unit 30 through first opening 45 to be described later, and second electrode 25 is electrically connected to sensing unit 30 through second opening 46 to be described later. First electrode 20 and second electrode 25 are disposed to face each other with insulating layer 40 therebetween. Note that sensing unit 30 may be disposed between first electrode 20 and second electrode 25 without insulating layer 40, and first electrode 20 and second electrode 25 may be disposed facing each other through sensing unit 30.

The materials of first electrode 20 and second electrode 25 are not particularly limited as long as being conductive materials. Each of first electrode 20 and second electrode 25 includes, for example, at least one metal selected from the group consisting of silver, gold, copper, platinum, and aluminum. The material of first electrode 20 may be the same as that of second electrode 25.

Note that the shape of each of first electrode 20 and second electrode 25 is not limited to an arc shape in plan view but may be, for example, a rod shape with an elongated rectangular shape in plan view or a comb shape in plan view. When the shape of each of first electrode 20 and second electrode 25 is a comb shape in plan view, for example, in first electrode 20 and second electrode 25, the teeth of one comb may be located between the teeth of the other comb.

Sensing unit 30 is an adsorption layer disposed above substrate so as to cover first electrode 20, second electrode 25, and insulating layer 40. Sensing unit 30 is formed of a member that changes in electrical characteristic, such as electric resistance, by adsorbing a chemical substance, such as a volatile organic compound, in a gas. Sensing unit 30 covers the entire upper surface and the entire side surface of insulating layer 40. Sensing unit 30 may only partially cover the upper surface and the side surface of insulating layer 40. Sensing unit 30 may cover the entire upper surface of substrate 10 or may partially cover the upper surface of substrate 10. Sensing unit 30 may or may not be in contact with substrate 10.

Sensing unit 30 is in contact with first electrode 20 through first opening 45 and is in contact with second electrode 25 through second opening 46. Thus, when a voltage is applied to first electrode and second electrode 25, a current flows through sensing unit 30. This enables the detection of the electrical characteristic, such as the electrical resistance, of sensing unit 30.

Sensing unit 30 is, for example, film-shaped. Thus, when the chemical substance is adsorbed onto sensing unit 30, the electrical characteristic is likely to change. The surface of sensing unit 30 opposite to substrate 10 side, that is, the upper surface of sensing unit 30, is exposed. The upper surface of sensing unit 30 is, for example, a flat surface but may be a curved surface. The thickness of sensing unit 30 is determined in accordance with the type of gas to be detected, the composition of sensing unit 30, and the like. The thickness of sensing unit 30 is, for example, in the range of 0.1 μm to 10 μm, inclusive. The shape of sensing unit 30 is not particularly limited. Sensing unit 30 has, for example, a circular shape or a ring shape in plan view. In the present embodiment, sensing unit 30 has a ring shape in plan view.

Sensing unit 30 may be porous. The area of sensing unit 30 in plan view is, for example, in the range of 0.002 mm$^2$ to 50 mm$^2$, inclusive.

Sensing unit 30 includes a conductive material and a polysiloxane compound as an adsorbent. In the present specification, the polysiloxane compound is an example of a polymer. With sensing unit 30 having the conductive material, a current can be allowed to flow through sensing unit 30. The electrical characteristic, such as the electrical resistance, of sensing unit 30 can be detected by allowing a current to flow through sensing unit 30. In sensing unit 30, for example, the conductive material is dispersed in the adsorbent.

The conductive material contained in sensing unit 30 is, for example, particles of the conductive material (that is, conductive particles). The average particle size of the particles of the conductive material may be in the range of 10 nm to 300 nm, inclusive. The "average particle size" can be measured by the following method. The surface or cross-section of sensing unit 30 is observed with an electron microscope, and the diameters of any number of particles (for example, 50 particles) contained in sensing unit 30 are measured. The average particle size is determined based on an average value calculated using the obtained measured values. The diameter of a circle having an area equal to the area of the particle observed with the electron microscope can be regarded as the particle size. Note that the conductive material may be a conductive material having a shape other than the shape of particles, such as fibers of the conductive material.

The conductive material is not particularly limited as long as having conductivity. The conductive material includes, for example, at least one selected from the group consisting of a carbon material, a conductive polymer, a metal material, a metal oxide, a semiconductor material, a superconductor, and a complex compound.

The carbon material includes, for example, at least one selected from the group consisting of carbon black, graphite, coke, carbon nanotube, graphene, and fullerene. The conductive polymer includes, for example, at least one selected from the group consisting of polyaniline, polythiophene, polypyrrole, and polyacetylene. The metal material includes, for example, at least one selected from the group consisting of silver, gold, copper, platinum, and aluminum. The metal oxide includes, for example, at least one selected from the group consisting of indium oxide, tin oxide, tungsten oxide, zinc oxide, and titanium oxide. The semiconductor material includes, for example, at least one selected from the group consisting of silicon, gallium arsenic, indium phosphide, and molybdenum sulfide. The superconductor includes, for example, at least one selected from the group consisting of $YBa_2Cu_3O_7$ and $Tl_2Ba_2Ca_2Cu_3O_{10}$. The complex compound includes, for example, at least one selected from the group consisting of a complex compound of tetramethylparaphenylenediamine and chloranil, a complex compound of tetracyanoquinodimethane and an alkali metal, a complex compound of tetrathiafulvalene and a halogen, a complex compound of iridium and a halocarbonyl compound, and tetracyanoplatinum.

The conductive material includes, for example, carbon black. When the conductive material contains carbon black, the electrical characteristic, such as the electrical resistance, of sensing unit 30 is likely to change. Hence the identification accuracy can be improved when gas sensor 100 is used to identify a chemical substance.

The ratio of the weight of the conductive material to the weight of sensing unit 30 need only be a ratio at which a current can be allowed to flow through sensing unit 30 by a pair of electrodes when the conductive material is connected. For example, the ratio may be in the range of 0.05 to 0.95, inclusive, or in the range of 0.25 to 0.95, inclusive. Thus, a current flows easily from first electrode 20 or second electrode 25 to sensing unit 30. This can facilitate the detection of the electrical characteristic, such as the electrical resistance, of sensing unit 30.

The polysiloxane compound adsorbs a chemical substance, such as a volatile organic compound, contained in a gas. The volume of sensing unit 30 changes due to the polysiloxane compound adsorbing the chemical substance in the gas. The polysiloxane compound has a siloxane bond as a main chain structure. That is, the polysiloxane compound has a polysiloxane structure as a main chain structure. The polysiloxane compound may have a linear polysiloxane structure as a main chain structure.

The polysiloxane compound has a cyano group in a side chain. With the cyano group being a hydrogen bond acceptor, the cyano group easily interacts with a hydrogen bond donor molecule, and when the gas contains hydrogen bond donor molecules, the electrical characteristic, such as the electrical resistance, of sensing unit 30 is likely to change. Hence the identification accuracy can be improved when gas sensor 100 is used to identify a chemical substance or the like.

The hydrogen bond donor molecule is, for example, a molecule having hydrogen capable of hydrogen bonding. The hydrogen bond donor molecule is, for example, an organic compound having at least one of an O—H bond, an N—H bond, and an S—H bond.

Further, the polysiloxane compound has an alkylene group, located between the cyano group and the main chain of the polysiloxane compound, in the side chain. For example, one end of the alkylene group is bonded to a silicon atom in the main chain of the polysiloxane compound, and the other end of the alkylene group is bonded to the cyano group. Thus, the cyano group can be separated from the main chain of the polysiloxane compound, so that the cyano group and the hydrogen bond donor molecule can more easily interact with each other. In general, the main chain of the linear polysiloxane structure is a helical structure, and the side chain of the polysiloxane compound is outside the helical structure. By the polysiloxane compound having the linear polysiloxane structure as the main chain structure and having the alkylene group in the side chain, the cyano group is further exposed outside of the helical structure, and hence the cyano group and the hydrogen bond donor molecule can easily interact with each other. Note that the polysiloxane compound may not have the alkylene group in the side chain.

The number of carbon atoms in the alkylene group is one or more, may be in one or more and ten or less, or may be two or more and five or less. The number of carbon atoms of the alkylene group may be three. That is, the polysiloxane compound may have a cyanopropyl group in the side chain. Thereby, the distance between the main chain and the cyano group in the polysiloxane compound is maintained appropriately, so that it is possible to achieve gas sensor 100 having both the stability of the polysiloxane compound and the identification accuracy when used to identify a chemical substance or the like. Examples of the siloxane structure (a repeating unit structure in the polysiloxane structure) contained in the polysiloxane compound having such a side chain include a biscyanopropylsiloxane structure, a cyanopropylmethyl structure, and a cyanopropylphenylsiloxane structure.

Note that the polysiloxane compound need only have the cyano group and the alkylene group in at least some side chains, and the polysiloxane compound need only have other substituents such as a hydrocarbon group in some side chains. At least one hydrogen atom of the alkylene group may be substituted with a substituent, such as a hydrocarbon group or a functional group containing a hetero element, or with an atom other than the hydrogen atom, such as a halogen atom.

The polysiloxane compound having the cyano group and the alkylene group in the side chains as thus described may specifically has at least one selected from the group consisting of a biscyanopropylpolysiloxane structure, a cyanopropylmethyl-dimethylpolysiloxane structure, a biscyanopropyl-cyanopropylphenylpolysiloxane structure, a cyanopropylphenyl-dimethylpolysiloxane structure, and a cyanopropylmethyl-phenylmethylpolysiloxane structure. Thus, sensing unit 30 can be achieved by the polysiloxane compound that is easy to synthesize.

Here, the term "cyanopropylmethyl-dimethylpolysiloxane structure" means a polysiloxane structure of a copolymer of cyanopropylmethylsiloxane and dimethylsiloxane, and the same applies to other polysiloxane structures. When the polysiloxane structure includes a copolymer, the copolymer may be a random copolymer, a block copolymer, or an alternating copolymer.

The polysiloxane compound may be a commercially available material. The polysiloxane compound may be synthesized by polymerizing alkoxysilanes such as dialkoxysilane, which are the units of the siloxane bond of the polysiloxane compound, through a condensation reaction.

For example, in the thermogravimetric analysis of the polysiloxane compound in an air atmosphere, a temperature at which the weight of the polysiloxane compound decreases by 5% or more relative to the weight of the polysiloxane compound at 35° C. may be 250° C. or higher. Thus, the polysiloxane compound has excellent thermal stability, so that a deterioration in the detection accuracy of gas sensor 100, for example, an increase in noise in the detection signal, over time is less likely to occur. Even at the time of heating during the drying of a solvent in the formation of sensing unit 30, which will be described later, sensing unit 30 is less likely to deteriorate, and the detection accuracy of gas sensor 100 can be improved. From the viewpoint of further improving the thermal stability of the polysiloxane compound, in the thermogravimetric analysis of the polysiloxane compound in the air atmosphere, the temperature at which the weight of the polysiloxane compound decreases by 5% or more relative to the weight of the polysiloxane compound at 35° C. may be 300° C. or higher. The thermogravimetric analysis is performed, for example, using a thermogravimetric analyzer under the condition that the temperature is increased from 35° C. to 400° C. at a temperature increase rate of 10° C./min in the air atmosphere.

The ratio of the weight of the polysiloxane compound to the weight of sensing unit 30 is determined in accordance with the type of gas to be detected, the type of conductive material, and the like. The ratio of the weight of the polysiloxane compound to the weight of sensing unit 30 may be in the range of 0.05 to 0.95, inclusive.

Sensing unit 30 may have an adsorbent other than the polysiloxane compound, which adsorbs the chemical substance in the gas.

Examples of the adsorbent other than the polysiloxane compound include a material that is commercially available as stationary phases of columns for gas chromatography. The adsorbent other than the polysiloxane compound includes, for example, at least one selected from the group consisting of polymeric materials and low molecular materials. The organic adsorbent includes, for example, at least one selected from the group consisting of polyalkylene glycols, polyesters, silicones other than the polysiloxane compound exemplified above, glycerols, nitriles, dicarboxylic acid monoesters, and aliphatic amines.

Polyalkylene glycols include, for example, polyethylene glycol. The polyesters include, for example, at least one selected from the group consisting of poly(diethylene glycol adipate) and poly(ethylene succinate). The silicones include, for example, at least one selected from the group consisting of dimethylpolysiloxane, phenylmethylpolysiloxane, diphenylpolysiloxane, phenylmethyl-dimethylpolysiloxane, phenylmethyl-diphenylpolysiloxane, trifluoropropylmethylpolysiloxane, and cyanopolysiloxane. Glycerols include, for example, diglycerol. The nitriles include, for example, at least one selected from the group consisting of N,N-bis(2-cyanoethyl) formamide and 1,2,3-tris(2-cyanoethoxy) propane. The dicarboxylic acid monoesters include, for example, at least one selected from the group consisting of nitroterephthalic acid-modified polyethylene glycol and diethylene glycol succinate. Aliphatic amines include, for example, tetrahydroxyethyl ethylenediamine.

Sensing unit 30 may further include an additive. Examples of the additive include a dispersant for improving the dispersibility of the conductive material.

The ratio of the weight of the polysiloxane compound to the weight of sensing unit 30 excluding the conductive material may be 0.85 or more, or 0.95 or more.

Insulating layer 40 covers each of first electrode 20 and second electrode 25. Insulating layer 40 is in contact with each of first electrode 20 and second electrode 25. Insulating layer 40 may cover the entire upper surface of substrate 10. Insulating layer 40 may partially cover the upper surface of substrate 10.

Insulating layer 40 has first opening 45 and second opening 46. First opening 45 exposes a part of the surface of first electrode 20. First opening 45 overlaps first electrode 20 in plan view. For example, the whole of first opening 45 overlaps first electrode 20 in plan view. First opening 45 penetrates insulating layer 40 in the thickness direction. Except for first opening 45, insulating layer 40 covers the entire upper surface and the entire side surface of first electrode 20.

Insulating layer 40 may have a plurality of first openings 45. The number of the plurality of first openings 45 is not particularly limited.

Second opening 46 exposes a part of the surface of second electrode 25. Second opening 46 overlaps second electrode 25 in plan view. For example, the whole of second opening 46 overlaps second electrode 25 in plan view. Second opening 46 penetrates insulating layer 40 in the thickness direction. Except for second opening 46, insulating layer 40 covers the entire upper surface and the entire side surface of second electrode 25.

Insulating layer 40 may have a plurality of second openings 46. The number of the plurality of second openings 46 is not particularly limited.

The shapes of first opening 45 and second opening 46 are not particularly limited. Each of first opening 45 and second opening 46 has, for example, a circular shape or a rectangular shape in plan view. As described above, first electrode 20 and second electrode 25, which are a pair of electrodes, are covered with insulating layer 40 and are electrically connected to sensing unit 30 through first opening 45 and second opening 46. By insulating layer 40 covering first electrode 20 and second electrode 25 as described above, the path of the current in sensing unit 30 is reduced, so that the electrical characteristic, such as the electric resistance, of sensing unit 30 to be detected change more greatly due to the change in the path of the current.

The material of insulating layer 40 is not particularly limited as long as having insulating properties. The material of insulating layer 40 includes, for example, at least one selected from the group consisting of an insulating polymeric material, ceramics, and glass. The insulating polymeric material includes, for example, at least one selected from the group consisting of polyethylene, polypropylene, polystyrene, polybutadiene, epoxy resin, fluorine resin, polyvinyl chloride, polymethyl methacrylate, polyamide, polyimide, polycarbonate, cellulose acetate, polyethylene terephthalate, polyethylene naphthalate, polyether sulfone, polyphenylene sulfide, and polyetherimide. The ceramic includes, for example, at least one selected from the group consisting of $SiO_2$, $Si_3N_4$, $Al_2O_3$, $Zr_2O_3$, and MgO.

Note that gas sensor 100 may not include insulating layer 40. In this case, for example, the upper surface and the side surface of each of first electrode 20 and second electrode 25 are in contact with and covered with sensing unit 30.

As illustrated in FIGS. 1 and 2, gas sensor 100 may further include first wall 11. First wall 11 surrounds the surface of substrate 10. First wall 11 has a ring shape in plan view. First wall 11 extends upward (in the thickness direction of substrate 10) from substrate 10. The surface of substrate 10 surrounded by first wall 11 has a circular shape, for example. First wall 11 is connected to the outer peripheral edge of substrate 10. First wall 11 may be integrated with substrate 10. In other words, first wall 11 may be a part of substrate 10. First wall 11 extends above sensing unit 30. The inner peripheral surface of first wall 11 is in contact with sensing unit 30.

Gas sensor 100 may further include second wall 12. Second wall 12 extends upward from a portion of the surface of substrate 10. The shape of second wall 12 is, for example, a columnar or cylindrical shape. Second wall 12 is connected to a part of the surface of substrate 10. Second wall 12 may be integrated with substrate 10. In other words, second wall 12 may be a part of substrate 10. Second wall 12 is surrounded by first electrode 20 and second electrode 25. Second wall 12 extends above sensing unit 30. The outer peripheral surface of second wall 12 is in contact with sensing unit 30. Sensing unit 30 is disposed between first wall 11 and second wall 12.

The material of first wall 11 and the material of second wall 12 are not particularly limited. Each of the material of first wall 11 and the material of second wall 12 may be hydrophobic. Each of the material of first wall 11 and the material of second wall 12 includes a hydrophobic polymeric material, for example. The hydrophobic polymeric material includes, for example, at least one selected from the group consisting of polyethylene, polypropylene, polystyrene, polybutadiene, epoxy resin, and fluorine resin. The material of first wall 11 may be the same as that of second wall 12. Each of the materials of first wall 11 and second wall 12 may be the same as the material of substrate 10.

Next, a method for manufacturing gas sensor 100 will be described.

First, each of first electrode 20 and second electrode 25 is disposed on substrate 10. A method for disposing each of first electrode 20 and second electrode 25 on substrate 10 is not particularly limited. For example, each of first electrode 20 and second electrode 25 can be disposed on substrate 10 by depositing metal on substrate 10. Examples of a method for depositing the metal include sputtering, ion plating, electron beam deposition, vacuum deposition, chemical vapor deposition, and chemical gas reaction.

Next, insulating layer 40 is formed. A method for producing insulating layer 40 is not particularly limited. Insulating layer 40 can be formed, for example, by the following method. A dispersion containing an insulating polymeric material is prepared. The dispersion is obtained by dispersing an insulating polymeric material in a coating solvent. The coating solvent includes, for example, at least one selected from the group consisting of water and an organic solvent.

The dispersion is applied in a desired pattern on substrate 10 so as to cover each of first electrode 20 and second electrode 25, thereby forming a coating film. As a method for forming the coating film, a printing method may be used. By drying the coating film, a precursor layer of insulating layer 40 is formed.

Next, first opening 45 and second opening 46 are formed in the precursor layer of insulating layer 40. This enables the formation of insulating layer 40. The method for forming first opening 45 and second opening 46 is not particularly limited. First opening 45 and second opening 46 can be formed, for example, by irradiating the precursor layer of insulating layer 40 with an ion beam. First opening 45 and second opening 46 can also be formed, for example, by etching the precursor layer of insulating layer 40.

Next, sensing unit 30 is formed. First, a coating solution containing a conductive material and a polysiloxane compound is prepared. The coating solution is obtained by dispersing a conductive material and a polysiloxane compound in a coating solvent. From the viewpoint of forming a uniform coating film, the polysiloxane compound may be dissolved in the coating solvent. The conductive material may be dissolved in the coating solvent. The coating solvent for forming sensing unit 30 includes, for example. at least one selected from the group consisting of water and an organic solvent. The organic solvent includes, for example, at least one selected from the group consisting of dimethyl sulfoxide, dimethyl formamide, toluene, chloroform, acetone, acetonitrile, methanol, ethanol, isopropanol, tetrahydrofuran, ethyl acetate, butyl acetate, and hexyl acetate. Next, the coating solution is applied on insulating layer 40 to form a coating film. By drying the coating film, sensing unit 30 is formed. The coating film is dried by being heated to, for example, 50° C. or higher and 200° C. or lower.

Sensing unit 30 formed by the method described above usually has a uniform thickness in the circumferential direction of the surface of substrate 10. In gas sensor 100 according to the present embodiment, first electrode 20 and second electrode 25 have an ark shape or a ring shape in plan view. Therefore, sensing unit 30 has a uniform thickness along first electrode 20. Similarly, sensing unit 30 has a uniform thickness along second electrode 25. This makes it possible to stably detect the electric resistance of sensing unit 30.

When gas sensor 100 is provided with first wall 11 and second wall 12, the dispersion can be applied uniformly. That is, the thickness of sensing unit 30 can be made uniform. When each of first wall 11 and second wall 12 has hydrophobicity, the surface tension generated between the dispersion and each of first wall 11 and second wall 12 is low. Therefore, the thickness of sensing unit can be made more uniform.

Next, a description will be given of an example of a method for detecting a chemical substance in a gas using gas sensor 100.

Figure 3:
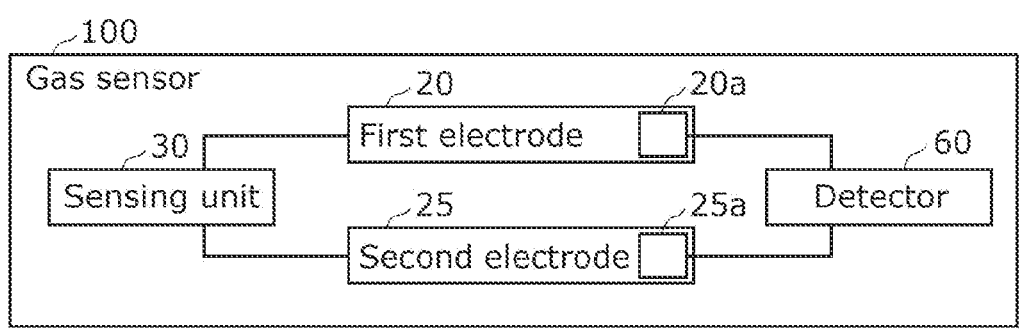
FIG. 3 is a block diagram illustrating a characteristic configuration of the gas sensor according to the embodiment.

FIG. 3 is a block diagram illustrating a characteristic configuration of gas sensor 100. As illustrated in FIG. 3, gas sensor 100 may further include detector 60.

Detector 60 is, for example, an electric resistance meter. Terminal 20a of first electrode 20 and terminal 25a of second electrode 25 are each connected to detector 60. Detector 60 can apply a voltage to first electrode 20 and second electrode 25, for example. When detector 60 applies a voltage to each of first electrode 20 and second electrode 25, a current flows through sensing unit 30. Detector 60 detects (in other words, measures) the electric resistance of sensing unit 30 based on the current flowing through sensing unit 30. Detector 60, for example, outputs the detected result as a detection signal to an external device. Detector 60 may have a display unit, such as a display or a meter for displaying the detected result.

In the detection of a chemical substance using gas sensor 100, first, gas sensor 100 is placed in a gas atmosphere. The gas contains, for example, a chemical substance containing at least one selected from the group consisting of a volatile organic compound and an inorganic gas. Examples of the volatile organic compound include ketones, amines, alcohols, aromatic hydrocarbons, aldehydes, esters, organic acids, methyl mercaptan, disulfide, and pyrrole. Examples of the inorganic gas include hydrogen sulfide, sulfur dioxide, and carbon disulfide.

When the chemical substance in the gas comes into contact with gas sensor 100, the polysiloxane compound of sensing unit 30 adsorbs the chemical substance. When the polysiloxane compound adsorbs the chemical substance, the volume of sensing unit 30 changes. Specifically, sensing unit 30 expands or contracts. A change in the volume of sensing unit 30 leads to a change in the positional relationship between the conductive materials in sensing unit 30. The path of the current changes due to the change in the positional relationship between the conductive materials, and the electrical characteristic such as the electrical resistance changes. For example, when sensing unit 30 adsorbs the chemical substance, sensing unit 30 expands, the contact between the conductive materials decreases, and the electric resistance of sensing unit 30 increases. Detector 60 detects the electrical characteristic, such as the electrical resistance, of sensing unit 30. Thus, gas sensor 100 can detect the chemical substance contained in the gas.

Note that gas sensor 100 may not be provided with detector 60, and the detection of the chemical substance in the gas as described above may be performed by connecting terminal 20a of first electrode and terminal 25a of second electrode 25 to an external detector.

Note that gas sensor 100 may detect the chemical substance from the value of the current flowing between first electrode 20 and second electrode 25 in a state where a constant voltage is applied between first electrode 20 and second electrode 25. Gas sensor 100 may detect the chemical substance from the amount of voltage drop between first electrode 20 and second electrode 25 in a state where a constant current is supplied to sensing unit 30. Detector 60 is, for example, a current meter or a voltage meter that measures a current or a voltage as described above. Detector 60 may output an index of the electric resistance of sensing unit 30 as a current signal or a voltage signal. That is, gas sensor 100 need only detect the chemical substance based on an index in accordance with a change in the electric resistance of sensing unit 30.

Next, a gas sensor assembly according to the present embodiment will be described.

Figure 4:
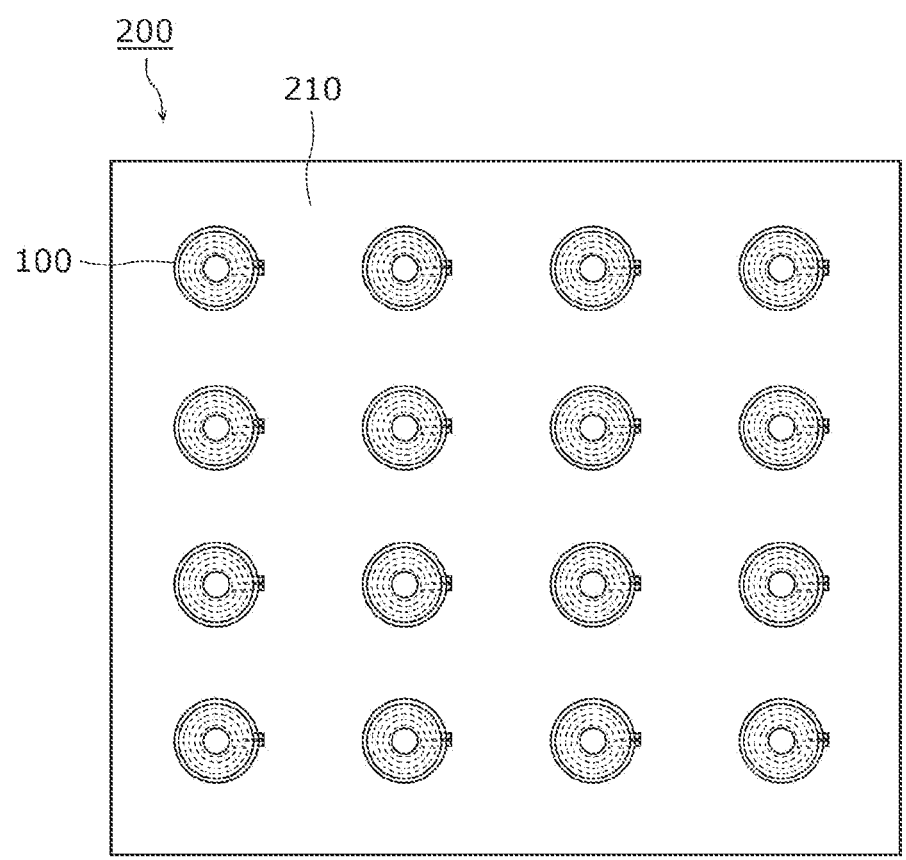
FIG. 4 is a plan view illustrating a schematic configuration of a gas sensor assembly according to the embodiment.

FIG. 4 is a plan view illustrating a schematic configuration of the gas sensor assembly according to the present embodiment. As illustrated in FIG. 4, gas sensor assembly 200 includes a plurality of gas sensors 100 and substrate 210.

Substrate 210 is, for example, plate-shaped. Substrate 210 has, for example, a rectangular shape in plan view. Substrate 210 has two pairs of end faces facing each other.

A plurality of gas sensors 100 are arranged on substrate 210. The sensing units 30 of at least two gas sensors 100 selected from the plurality of gas sensors 100 may be made of different materials. Specifically, the types of polysiloxane compounds contained in the respective sensing units 30 of at least two gas sensors 100 selected from the plurality of gas sensors 100 may be different from each other. The types of polysiloxane compounds contained in the respective sensing units 30 of all the plurality of gas sensors 100 may be different from each other. In this case, two or more gas sensors 100 provided with the sensing units 30 containing different types of polysiloxane compounds exhibit different behaviors relative to a specific chemical substance. For example, a chemical substance that is hardly adsorbed onto specific gas sensor 100 is easily adsorbed onto other gas sensors 100. Hence the identification accuracy can be improved when gas sensor assembly 200 (that is, the plurality of gas sensors 100) is used to identify a chemical substance or the like.

The number of the plurality of gas sensors 100 provided in gas sensor assembly 200 is not particularly limited. The number of the plurality of gas sensors 100 provided in gas sensor assembly 200 is set in accordance with the type of chemical substance to be detected or identified. As illustrated in FIG. 4, the number of the plurality of gas sensors 100 is, for example, 16. In FIG. 4, four gas sensors 100 are arranged in a direction from one of a pair of end surfaces of substrate 210 toward the other. Four gas sensors 100 are arranged in a direction from one of the other pair of end faces of substrate 210 toward the other. In other words, the plurality of gas sensors 100 are arranged in a matrix of four rows and four columns. Note that the arrangement of the plurality of gas sensors 100 is not particularly limited.

The plurality of gas sensors provided in gas sensor assembly 200 need only include at least one gas sensor 100. For example, gas sensor assembly 200 may include, in addition to gas sensor 100, a gas sensor provided with a sensing unit having, instead of the above-described polysiloxane compound of gas sensor 100, an adsorbent other than the polysiloxane compound. Examples of the adsorbent other than the polysiloxane compound include the adsorbents other than the polysiloxane compound exemplified above.

Figure 5:
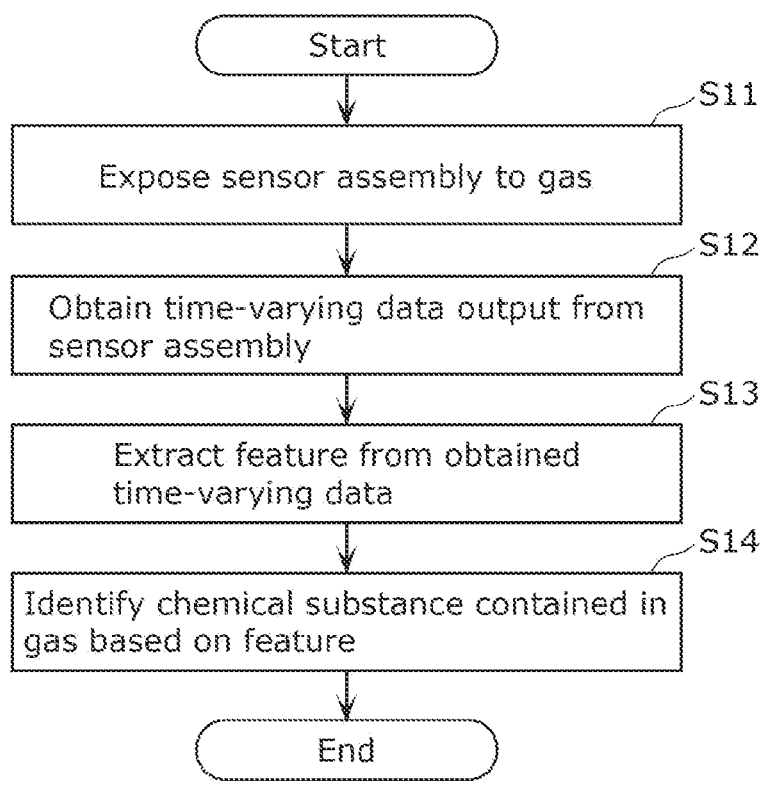
FIG. 5 is a flowchart of a chemical substance identification method using the gas sensor assembly according to the embodiment.

Next, a description will be given of an example of a method for identifying a chemical substance in a gas using gas sensor assembly 200 according to the present embodiment. FIG. 5 is a flowchart of a chemical substance identification method using gas sensor assembly 200 according to the present embodiment.

First, gas sensor assembly 200 is exposed to a gas containing a chemical substance (step S11). For example, gas sensor assembly 200 is placed in a stream of an inert gas such as nitrogen. Then, the chemical substance is mixed into the gas stream for a certain period of time. Gas sensor assembly 200 may be disposed in a closed container connected to a pipe, and an inert gas such as nitrogen and a gas containing a chemical substance may be exclusively introduced into the closed container through the pipe. In this manner, gas sensor assembly 200 is exposed to the gas containing the chemical substance. The gas includes, for example, a volatile organic compound as a chemical substance. The volatile organic compound may be a hydrogen bond donor molecule.

Next, the time-varying data output from gas sensor assembly 200 exposed to the gas containing the chemical substance is obtained (step S12). The time-varying data is an example of a signal output from the gas sensor assembly. For example, detector 60 obtains the electric resistance or the like of sensing unit 30 during a period including before and after the mixing of the chemical substance and outputs the obtained electric resistance or the like as a signal including the time-varying data. The output signal is, for example, a voltage signal or a current signal. Thus, for example, the time-varying data of the electric resistance or the like of sensing unit 30 output from detector 60 can be obtained for each of the plurality of gas sensors 100.

Next, from the time-varying data obtained in step S12, a feature for use in the identification of the chemical substance is calculated (step S13). Specifically, the feature of the time-varying data corresponding to each of the plurality of gas sensors 100 is calculated from the obtained time-varying data. The feature is, for example, the difference or ratio between the electric resistance during when the chemical substance is mixed and the electric resistance during when the chemical substance is not mixed. The feature is not limited to the difference or ratio of the electric resistance but may be the amount of change per time of the electric resistance at the start of mixing of the chemical substance or at the end of mixing of the chemical substance, that is, an inclination of the electric resistance in the time-varying data. A feature (for example, an eigenvalue obtained by the principal component analysis of the time-varying data) based on the waveform of the time-varying data obtained when the chemical substance is mixed may be used. Depending on the type of output signal, a value such as a voltage or a current may be used to calculate the feature instead of the electric resistance. The number of features to be calculated is not particularly limited but may be one for each gas sensor 100 or a plurality for each gas sensor 100. As described above, a feature related to a change in the electrical characteristic of sensing unit 30 of gas sensor 100 due to the mixing of the chemical substance can be used to identify the chemical substance.

Next, the chemical substance contained in the gas is identified based on the feature calculated in step S13 using a logical model for identifying the chemical substance (step S14). For example, by using a computer or the like, the chemical substance is identified by inputting the feature calculated from the time-varying data that is the detection result of gas sensor assembly 200 (that is, the feature corresponding to each of the plurality of gas sensors 100) into the logical model for use in the identification of the chemical substance. The logical model is a learned logical model that has been learned in advance by machine learning. For example, the logical model outputs, as an identification result, which of a plurality of chemical substances to be identified is the chemical substance contained in the gas. The plurality of chemical substances to be identified include, for example, a hydrogen bond donor molecule.

The logical model for use in the identification of the chemical substance is constructed by machine learning using a feature calculated for a known chemical substance by using, for example, a computer or the like. For example, for each of the plurality of chemical substances to be identified, a feature corresponding to each of the plurality of gas sensors 100 is calculated by the same method as in step S13. That is, for each chemical substance, features are calculated as many as the number of the plurality of gas sensors 100. Then, a logical model is constructed by performing machine learning, using the calculated features as explanatory variables in teacher data. The method used for constructing a logical model in machine learning is not particularly limited. For example, a random forest is used to construct a logical model in machine learning. A neural network, support vector machine, or self-organizing map may be used to construct a logical model in machine learning.

Note that the method for identifying the chemical substance is not limited to the method described above but may be a method using discriminant analysis other than machine learning, such as cluster analysis, genetic algorithm, or k-means method. The identification method described above may be applied to odor identification or intensity detection using gas sensor assembly 200.

Gas sensor assembly 200 may include a processing unit that performs the processing from step S12 to step S14. The processing unit is achieved by a microcomputer, a processor, or the like that incorporates a program for performing the processing.

Instead of gas sensor assembly 200, one or more gas sensors 100 may be used to identify the chemical substance in the manner described above.

EXAMPLE

The present disclosure will be described in detail based on an example. However, the present disclosure is not in any way limited by the following example. In the description of the following example, benzaldehyde may be referred to as "Bz", nonanal may be referred to as "Nn", and pyrrole may be referred to as "Pr".

(Production of Gas Sensor)
[Sample 1]

A gas sensor of Sample 1 was produced so as to have a structure similar to that of gas sensor 100 illustrated in FIGS. 1 and 2. Specifically, first, each of a first electrode and a second electrode was disposed on a substrate having a circular shape in plan view. Platinum was used for each of the first electrode and the second electrode, and a silicon substrate was used as a substrate.

Next, each of the first electrode and the second electrode was covered with a precursor layer of an insulating layer. $SiO_2$ was used as a material of the precursor layer. An insulating layer was produced by providing four first openings and four second openings in the precursor layer. Each of the first opening and the second opening had a circular shape in plan view. The diameter of each of the first opening and the second opening in plan view was 5 μm.

Next, a coating solution containing a conductive material and an adsorbent as a material of a sensing unit was applied to the insulating layer in a circular shape to form a coating film. Hexyl acetate and dimethylformamide were used as solvents for the coating solution. As the conductive material, carbon black was used. As the adsorbent, cyanopropylmethyl-dimethylpolysiloxane (manufactured by GL Sciences Inc., trade name OV-105), which is a polysiloxane compound having a cyanopropyl group in a side chain, was used. The coating film was dried at 140° C. to form the sensing unit. The ratio of the weight of the conductive material to the weight of the sensing unit was 0.5. The diameter of the sensing unit was 900 μm. The gas sensor of Sample 1 was obtained in this manner.

[Sample 2]

A gas sensor was produced by the same method as in Sample 1 except that cyanopropylphenyl-dimethylpolysiloxane (manufactured by GL Sciences Inc., trade name OV-1701), which is a polysiloxane compound having a cyanopropyl group in a side chain, was used as the adsorbent of the sensing unit, and a gas sensor of Sample 2 was obtained.

[Sample 3]

A gas sensor was produced by the same method as in Sample 1 except that cyanopropylmethyl-phenylmethylpolysiloxane (manufactured by GL Sciences Inc., trade name OV-225), which is a polysiloxane compound having a cyanopropyl group in a side chain, was used as the adsorbent of the sensing unit, and a gas sensor of Sample 3 was obtained.

[Sample 4]

A gas sensor was produced by the same method as in Sample 1 except that biscyanopropyl-cyanopropylphenylpolysiloxane (manufactured by Sigma-Aldrich Co., trade name SP-2330), which is a polysiloxane compound having a cyanopropyl group in a side chain, was used as the adsorbent of the sensing unit, and a gas sensor of Sample 4 was obtained.

[Sample 5]

A gas sensor was produced by the same method as in Sample 1 except that biscyanopropylpolysiloxane (manufactured by Sigma-Aldrich Co., trade name SP-2340), which is a polysiloxane compound having a cyanopropyl group in a side chain, was used as the adsorbent of the sensing unit, and a gas sensor of Sample 5 was obtained.

[Sample 6]

A gas sensor was produced by the same method as in Sample 1 except that biscyanopropylpolysiloxane (manufactured by GL Sciences Inc., trade name OV-275), which is a polysiloxane compound having a cyanopropyl group in a side chain, was used as the adsorbent of the sensing unit, and a gas sensor of Sample 6 was obtained.

[Sample 7]

A gas sensor was produced by the same method as in Sample 1 except that dimethylpolysiloxane (manufactured by GL Sciences Inc., trade name OV-101), which is a polysiloxane compound having a side chain containing a hydrocarbon group, was used as the adsorbent of the sensing unit, and a gas sensor of Sample 7 was obtained.

[Sample 8]

A gas sensor was produced by the same method as in Sample 1 except that phenylmethyl-dimethylpolysiloxane (manufactured by GL Sciences Inc., phenyl ratio 10%, trade name OV-3), which is a polysiloxane compound having side chains containing hydrocarbon groups, was used as the adsorbent of the sensing unit, and a gas sensor of Sample 8 was obtained.

[Sample 9]

A gas sensor was produced by the same method as in Sample 1 except that phenylmethyl-dimethylpolysiloxane (manufactured by GL Sciences Inc., phenyl ratio 20%, trade name OV-7), which is a polysiloxane compound having a side chain containing a hydrocarbon group, was used as the adsorbent of the sensing unit, and a gas sensor of Sample 9 was obtained.

[Sample 10]

A gas sensor was produced by the same method as in Sample 1 except that phenylmethyl-dimethylpolysiloxane (manufactured by GL Sciences Inc., phenyl ratio 50%, trade name OV-17), which is a polysiloxane compound having a side chain containing a hydrocarbon group, was used as the adsorbent of the sensing unit, and a gas sensor of Sample 10 was obtained.

[Sample 11]

A gas sensor was produced by the same method as in Sample 1 except that phenylmethyl-diphenylpolysiloxane (manufactured by GL Sciences Inc., phenyl ratio: 65%, trade name: OV-22), which is a polysiloxane compound having a side chain containing a hydrocarbon group, was used as the adsorbent of the sensing unit, and a gas sensor of Sample 11 was obtained.

[Sample 12]

A gas sensor was produced by the same method as in Sample 1 except that phenylmethyl-diphenylpolysiloxane (manufactured by GL Sciences Inc., phenyl ratio 75%, trade name OV-25), which is a polysiloxane compound having side chains containing a hydrocarbon group, was used as the adsorbent of the sensing unit, and a gas sensor of Sample 12 was obtained.

[Sample 13]

A gas sensor was produced by the same method as in Sample 1 except that N,N-bis(2-cyanoethyl) formamide was used as the adsorbent of the sensing unit, and a gas sensor of Sample 13 was obtained.

(Thermogravimetric Analysis)

Figure 6:
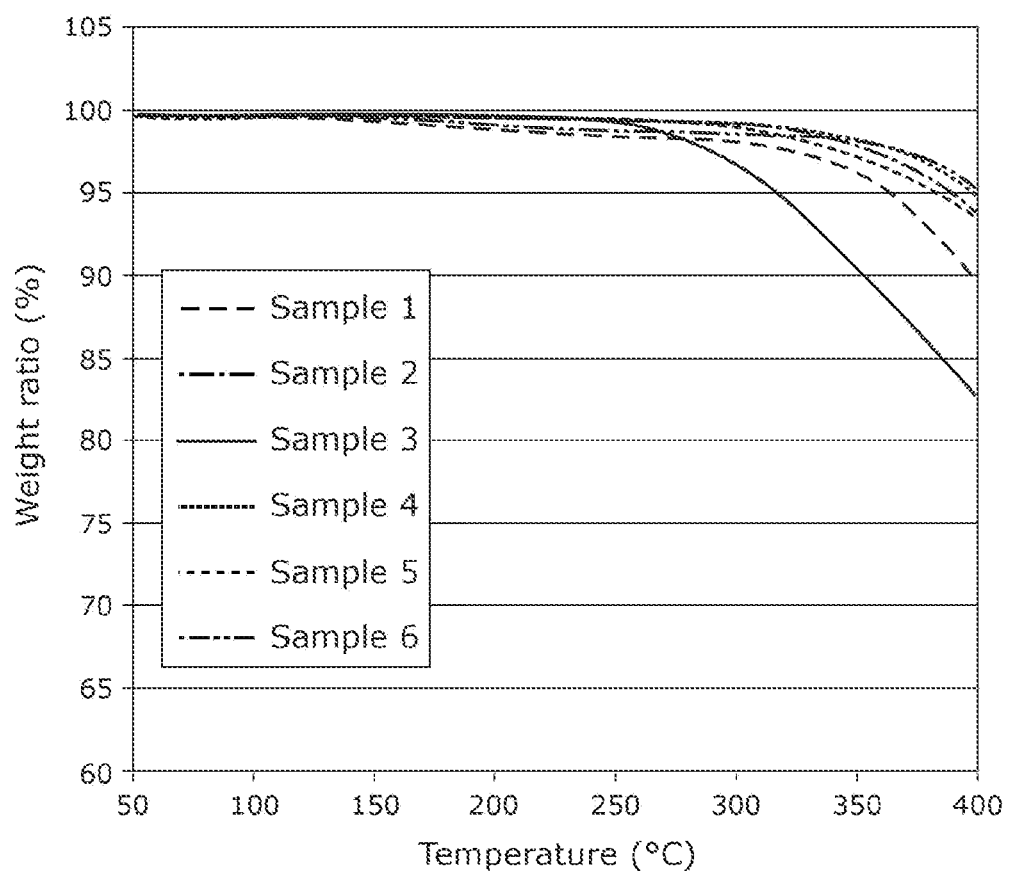
FIG. 6 is a diagram illustrating a result of a thermogravimetric analysis of an adsorbent in each of sensing units in gas sensors of Samples 1 to 6.
Figure 7:
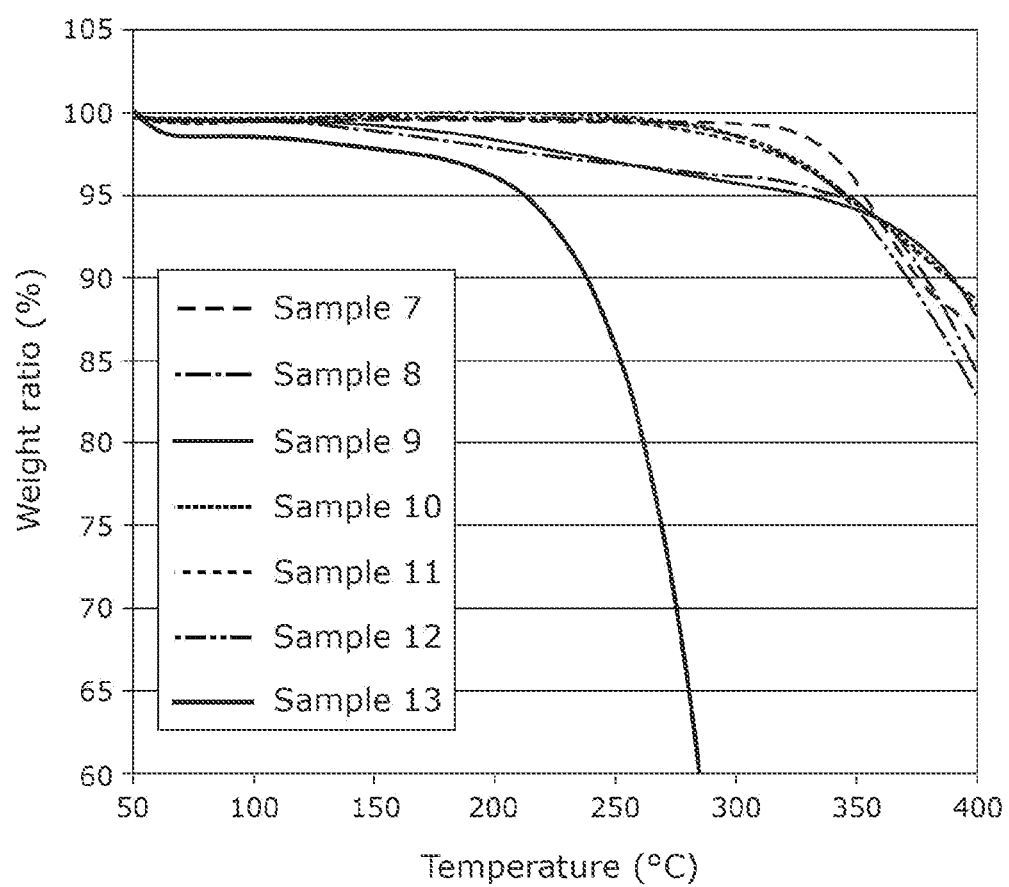
FIG. 7 is a diagram illustrating a result of a thermogravimetric analysis of an adsorbent in each of sensing units in gas sensors of Samples 7 to 13.

Thermogravimetric analysis was performed on the adsorbents of the sensing units in the gas sensors of Samples 1 to 13. Specifically, the thermogravimetric analysis was performed using a thermogravimetric analyzer under the condition that the temperature is increased from 35° C. to 400° C. at a temperature increase rate of 10° C./min in an air atmosphere. FIG. 6 illustrates the results of the thermogravimetric analysis of the adsorbents of the sensing units in the gas sensors of Samples 1 to 6. FIG. 7 illustrates the results of the thermogravimetric analysis of the adsorbents of the sensing units in the gas sensors of Samples 7 to 13. In FIGS. 6 and 7, the horizontal axis represents the temperature, and the vertical axis represents the weight ratio to the weight of the adsorbent at 35° C.

As illustrated in FIGS. 6 and 7, for each of the adsorbents of the sensing units in the gas sensors of Samples 1 to 12, the temperature at which the weight of the adsorbent decreased by 5% or more relative to the weight of the adsorbent at 35° C. was 250° C. or higher. In contrast, for the adsorbent of the sensing unit in the gas sensor of Sample 13, the temperature at which the weight of the adsorbent decreased by 5% or more relative to the weight of the adsorbent at 35° C. was lower than 250° C. As described above, the results were obtained showing that the polysiloxane compounds serving as the adsorbents of the sensing units in the gas sensors of Samples 1 to 12 have high thermal stability.

(Evaluation of Changes in Detection Results)

For the gas sensor of Sample 5 and the gas sensor of Sample 13, changes in detection results of chemical substances in the gas were evaluated zero days after the gas sensor production (that is, the day of the gas sensor production) and six months after the gas sensor production. The gas sensor was stored at room temperature in the atmosphere.

Figure 8:
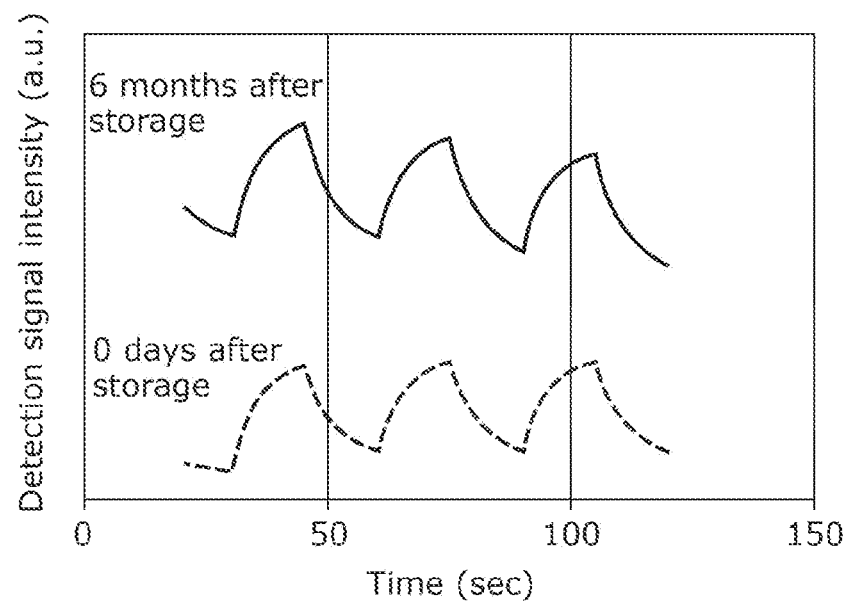
FIG. 8 is a diagram illustrating the detection results of the gas sensor of Sample 5.
Figure 9:
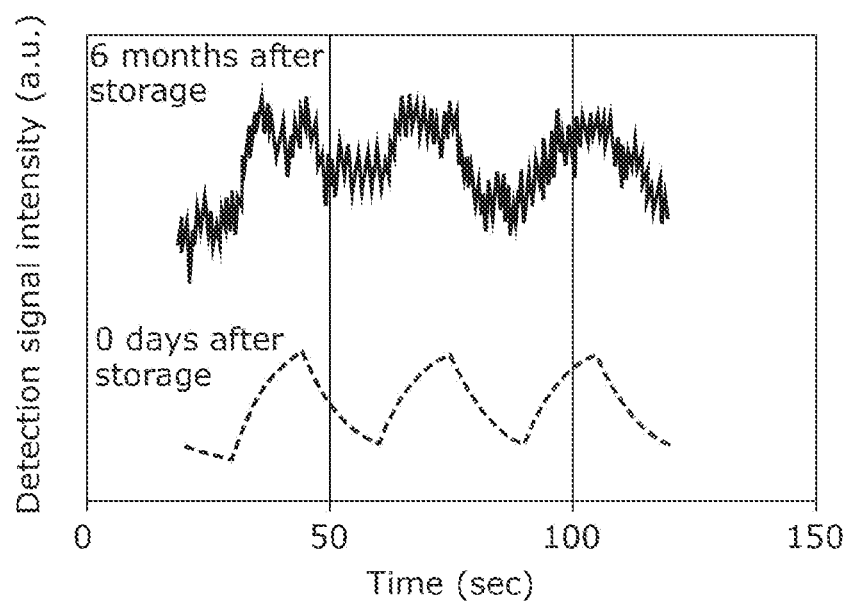
FIG. 9 is a diagram illustrating the detection results of the gas sensor of Sample 13.

In the evaluation of the detection results, a detector for detecting electric resistance was connected to the gas sensor, and a detection signal of the electric resistance of the gas sensor was obtained. Specifically, the gas sensor was placed in a nitrogen stream, and the detection signal of the electric resistance of the gas sensor was obtained from the detector during the repetition of the mixing of benzaldehyde as the chemical substance in the gas stream at a concentration of 2 ppm for 15 seconds and the flowing of a nitrogen-only gas stream for 15 seconds. In other words, the time-varying data of the electric resistance of the gas sensor was obtained. FIG. 8 illustrates the detection results of the gas sensor of Sample 5, and FIG. 9 illustrates the detection results of the gas sensor of Sample 13. In FIGS. 8 and 9, the horizontal axis represents the elapsed time, and the vertical axis represents the standardized detection signal intensity (that is, an index of the electric resistance of the sensing unit). In each of FIGS. 8 and 9, a broken-line graph shows the detection result zero days after the gas sensor production, and a solid-line graph illustrates the detection result six months after the gas sensor production. In each of FIGS. 8 and 9, the graph of the detection result after six months has been slid upward for ease of viewing.

As illustrated in FIG. 8, in the gas sensor of Sample 5, time-varying data with small noise was obtained in both detection results after zero days and after six months from the gas sensor production. In contrast, as illustrated in FIG. 9, in the gas sensor of Sample 13, time-varying data with large noise was obtained in the detection result after six months from the gas sensor production. As described above, it has been found that the gas sensor of Sample 5 provided with the sensing unit containing the adsorbent, in which the weight of the adsorbent decreases by 5% or more relative to the weight of the adsorbent at 35° C. at a temperature of 250° C. or higher, produces a detection result with small noise even when stored for a long period of time.

(Production of Gas Sensor Assembly)

A gas sensor assembly was produced by using the gas sensors of Samples 1 to 12.

[Sample 14]

On a silicon substrate having a rectangular shape in plan view, the gas sensors of Samples 1 to 6, that is, six gas sensors in total, were arranged in a matrix form of two rows and three columns. The gas sensor assembly of Sample 14 was obtained in this manner. Further, a detector for detecting electric resistance was connected to each of six gas sensors (that is, the gas sensors of Samples 1 to 6) provided in the gas sensor assembly of Sample 14. One detector was connected to one gas sensor.

[Sample 15]

On a silicon substrate having a rectangular shape in plan view, the gas sensors of Samples 7 to 12, that is, six gas sensors in total, were arranged in a matrix form of two rows and three columns. The gas sensor assembly of Sample 15 was obtained in this manner. Further, a detector for detecting electric resistance was connected to each of six gas sensors (that is, the gas sensors of Samples 7 to 12) provided in the gas sensor assembly of Sample 15. One detector was connected to one gas sensor.

(Identification of Chemical Substances)

Example 1

(1) Obtainment of Features

First, the gas sensor assembly of Sample 14 was placed in a nitrogen stream, benzaldehyde as the chemical substance was mixed into the gas stream at a concentration of 2 ppm for 30 seconds, and the electric resistance of the gas sensor from 30 seconds before the start of chemical substance mixing to 30 seconds after the end of chemical substance mixing was obtained from the detector. Thus, the time-varying data of the electric resistance was obtained for each of the sensing units of the gas sensors of Samples 1 to 6. For each of the obtained six time-varying data, an electric resistance value "a" before the start of the mixing of the chemical substance, an electric resistance value "b" during the mixing of the chemical substance, and an electric resistance value "c" at a time when a predetermined time has elapsed after the end of the mixing of the chemical substance were obtained. From the obtained electric resistance values "a", "b", and "c", a feature R ($R=b/(a/2+c/2)$), which is a ratio of an average value of the electric resistance value "a" and the electric resistance value "b" to the electric resistance value "c" was calculated. That is, for benzaldehyde, six features R were obtained as one set of features R corresponding to the respective gas sensors of Samples 1 to 6.

This operation of obtaining the time-varying data was repeated 30 times, and 30 sets of characteristic quantities R corresponding to the respective gas sensors of Samples 1 to 6 were obtained for benzaldehyde.

Next, benzaldehyde was replaced with each of nonanal and pyrrole as the chemical substance, and the same operation as described above was performed. As a result, 30 sets of features R corresponding to the gas sensors of Samples 1 to 6 were obtained for nonanal, and 30 sets of features R corresponding to the gas sensors of Samples 1 to 6 were obtained for pyrrole.

Of benzaldehyde, nonanal, and pyrrole, benzaldehyde and nonanal are hydrogen bond acceptor molecules, and pyrrole is a hydrogen bond donor molecule.

(2) Construction of Logical Model

A logical model was constructed by machine learning using five sets of features R arbitrarily selected from the 30 sets of features R for each of benzaldehyde, nonanal, and pyrrole obtained in "(1) Obtainment of Features". For constructing a logical model in machine learning, a random forest using six features R corresponding to the respective gas sensors of Samples 1 to 6 for conditional branching was used. In this manner, the logical model of the random forest for identifying the chemical substance was constructed by performing machine learning using five sets of features R for each of benzaldehyde, nonanal, and pyrrole as explanatory variables in teacher data.

(3) Identification of Chemical Substance

Of the 30 sets of features R for each of benzaldehyde, nonanal, and pyrrole obtained in "(1) Obtainment of Features" above, 25 sets of features R not used in "(2) Construction of Logical Model" above were used to identify the chemical substance. Specifically, the chemical substance was identified by the constructed logical model from 25 sets of features R for each of benzaldehyde, nonanal, and pyrrole. That is, the identification of the chemical substance was performed times for each of benzaldehyde, nonanal, and pyrrole. Table 1 shows the results of the identification.

In Table 1, each cell shows the number of times that the chemical substance (Bz, Nn, or Pr), listed at the left-most part of the row where the cell is located, was identified by the constructed logical model when the feature R calculated from the detection result of the mixing of the chemical substance (Bz, Nn, or Pr), listed at the top of the column where the cell is located, was input. In other words, the numerical value of the cell for which the chemical substances listed in the top and the left-most part are the same is the number of times the identification was correct, and the numerical value of the cell for which the chemical substances listed in the top and the left-most part are different is the number of times the identification was incorrect. These are also the same in Table 2 to be described later.

TABLE 1

| | | Mixed chemical substance | | |
|---|---|---|---|---|
| | | Bz | Nn | Pr |
| Identification Result | Bz | 25 | 0 | 0 |
| | Nn | 0 | 25 | 0 |
| | Pr | 0 | 0 | 25 |

As shown in Table 1, in Example 1, the mixed chemical substance and the identified chemical substance matched all the 25 times for each of all the three chemicals. The ratio of the number of times the correct identification result was obtained (75 times) to the total number of times each chemical substance was identified (75 times) was 100%. As thus described, when the chemical substances were identified using the gas sensors of Samples 1 to 6 each containing the polysiloxane compound having the cyanopropyl group in the side chain as the adsorbent of the sensing unit, good identification results were obtained. That is, in Example 1, the identification accuracy in the case of identifying the chemical substance is high by using the gas sensor assembly of Sample 14 (that is, the gas sensors of Samples 1 to 6).

Comparative Example 1

Chemical substances were identified in the same manner as in "(1) Obtainment of feature" to "(3) Identification of Chemical Substances" in Example 1, except that the gas sensor assembly of Sample 15 was placed in the nitrogen stream as the gas sensor assembly. Table 2 shows the results of the identification.

TABLE 2

| | | Mixed chemical substance | | |
|---|---|---|---|---|
| | | Bz | Nn | Pr |
| Identification Result | Bz | 25 | 0 | 16 |
| | Nn | 0 | 25 | 0 |
| | Pr | 0 | 0 | 9 |

In Comparative Example 1, when pyrrole was mixed as the chemical substance, benzaldehyde was identified 16 times out of 25 times, and pyrrole was identified only 9 times. The ratio of the number of times the correct identification result was obtained (59 times) to the total number of times each chemical substance was identified (75 times) was 79%. As thus described, when chemical substances were identified using the gas sensors of Samples 7 to 12 each containing the polysiloxane compound having the hydrocarbon group in the side chain as the adsorbent of the sensing unit, good identification results were not obtained for pyrrole, which is a hydrogen bond donor molecule.

Although the gas sensor and the like according to the present disclosure have been described based on the embodiment and example, the present disclosure is not limited to the embodiment and example. Ones obtained by applying various modifications conceivable by a person skilled in the art to the embodiment and example and another form constructed by combining some components of the embodiment and example is also within the scope of the present disclosure as long as not departing from the spirit of the present disclosure.

INDUSTRIAL APPLICABILITY

The gas sensor, gas sensor assembly, and chemical substance identification method according to the present disclosure are useful for detecting or identifying a chemical substance or the like in a gas.

The invention claimed is:

1. A gas sensor comprising:
a sensing unit; and
a pair of electrodes each electrically connected to the sensing unit, wherein:
the sensing unit includes:
conductive material; and
a polymer including a siloxane bond as a main chain structure, the polymer includes, in a side chain:
a cyano group; and
an alkylene group located between the cyano group and the main chain, and
the gas sensor is used to detect a hydrogen bond donor molecule.

2. The gas sensor according to claim 1, wherein
the polymer includes a cyanopropyl group in the side chain.

3. The gas sensor according to claim 1, wherein
the polymer includes at least one structure selected from the group consisting of a biscyanopropylpolysiloxane structure, a cyanopropylmethyl-dimethylpolysiloxane structure, a biscyanopropyl-cyanopropylphenylpolysiloxane structure, a cyanopropylphenyl-dimethylpolysiloxane structure, and a cyanopropylmethyl-phenylmethylpolysiloxane structure.

4. The gas sensor according to claim 1, wherein
in a thermogravimetric analysis of the polymer in an air atmosphere, a temperature at which a weight of the polymer decreases by 5% or more relative to the weight of the polymer at 35° C. is 250° C. or higher.

5. The gas sensor according to claim 1, further comprising a detector that detects electric resistance of the sensing unit.

6. The gas sensor according to claim 1, wherein
the conductive material is conductive particles, and
an average particle size of the conductive particles is in the range of 10 nm to 300 nm, inclusive.

7. The gas sensor according to claim 1, wherein
a ratio of a weight of the conductive material to a weight of the sensing unit is in the range of 0.05 to 0.95, inclusive.

8. The gas sensor according to claim 1, wherein
the sensing unit is film-shaped.

9. A gas sensor assembly comprising:
a plurality of gas sensors,
wherein at least one of the plurality of gas sensors is the gas sensor according to claim 1.

10. A chemical substance identification method using the gas sensor assembly according to claim 9, the chemical substance identification method comprising:
obtaining a signal output from the gas sensor assembly exposed to a gas containing a chemical substance;
calculating a feature value from the signal obtained; and
identifying whether the chemical substance contained in the gas comprises a hydrogen bond donor molecule by comparing the feature value with a predetermined feature value for the hydrogen bond donor molecule.

11. The chemical substance identification method according to claim 10, wherein:
the gas sensor further comprises a detector that detects electric resistance of the sensing unit, and the obtaining the signal output from the gas sensor assembly comprises obtaining a time-varying data of the electric resistance.

12. The chemical substance identification method according to claim 11, wherein:

the identifying the chemical substance contained in the gas comprises inputting the feature value calculated from the time-varying data into a logical model.

13. The chemical substance identification method according to claim 12, wherein:

the logical model outputs, as an identification result, which of a plurality of chemical substances to be identified is the chemical substance contained in the gas.

14. The chemical substance identification method according to claim 12, wherein:

the logical model comprises a learned logical model that has been learned by machine learning.

15. A detection method for detecting a hydrogen bond donor molecule by using the gas sensor according to claim 1, the detection method comprising:

obtaining a signal output from the gas sensor;
calculating a feature value from the signal obtained; and
detecting the hydrogen bond donor molecule contained in the gas by comparing the feature value with a predetermined feature value for the hydrogen bond donor molecule.

16. The detection method according to claim 15, wherein:

the gas sensor further comprises a detector that detects electric resistance of the sensing unit, and
the obtaining the signal output from the gas sensor assembly comprises obtaining a time-varying data of the electric resistance.

17. The detection method according to claim 16, wherein:

the identifying the chemical substance contained in the gas comprises inputting the feature value calculated from the time-varying data into a logical model.

18. The detection method according to claim 17, wherein:

the logical model outputs, as an identification result, which of a plurality of chemical substances to be identified is the chemical substance contained in the gas.

19. The detection method according to claim 17, wherein:

the logical model comprises a learned logical model that has been learned by machine learning.

* * * * *